US010226232B2

(12) United States Patent
Van de Wardt et al.

(10) Patent No.: US 10,226,232 B2
(45) Date of Patent: Mar. 12, 2019

(54) BRACHYTHERAPY INSTRUMENT, AN IMAGING SYSTEM AND A METHOD OF IMAGE ACQUISITION

(71) Applicant: Nucletron Operations B.V., Veenendaal (NL)

(72) Inventors: Cor Van de Wardt, Veenendaal (NL); Wilhelmus Petra Martinus Maria Van Erp, Veenendaal (NL); Luite Visscher, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 374 days.

(21) Appl. No.: 14/651,541

(22) PCT Filed: Dec. 11, 2013

(86) PCT No.: PCT/NL2013/050889
§ 371 (c)(1),
(2) Date: Jun. 11, 2015

(87) PCT Pub. No.: WO2014/092570
PCT Pub. Date: Jun. 19, 2014

(65) Prior Publication Data
US 2015/0327949 A1    Nov. 19, 2015

Related U.S. Application Data

(60) Provisional application No. 61/737,313, filed on Dec. 14, 2012.

(30) Foreign Application Priority Data

Dec. 12, 2012 (NL) .................................. 2009974

(51) Int. Cl.
*A61B 8/00* (2006.01)
*A61B 8/08* (2006.01)
(Continued)

(52) U.S. Cl.
CPC .............. *A61B 8/481* (2013.01); *A61B 5/055* (2013.01); *A61B 8/0841* (2013.01);
(Continued)

(58) Field of Classification Search
CPC .............................. A61N 5/1027; A61K 51/00
See application file for complete search history.

(56) References Cited

U.S. PATENT DOCUMENTS 6,083,167 A * 7/2000 Fox ...................... A61N 5/1002
                                                    600/439
6,311,084 B1 10/2001 Cormack et al.
(Continued)

FOREIGN PATENT DOCUMENTS

| DE | 102008045988 A1 | 3/2010 |
| EP | 1559363 A2 | 8/2005 |
| WO | WO-2005/0074797 A1 | 8/2005 |

OTHER PUBLICATIONS

Frank, Steven J. et al., "A Novel MRI Marker for Prostate Brachytherapy," *International Journal of Radiation Oncology Biology Physics*, vol. 71, Issue 1, May 2008, 5-8 (4 pages).
International Preliminary Report on Patentability for International Application No. PCT/NL2013/050889, dated Mar. 9, 2015 (8 pages).
International Search Report and Written Opinion for International Application No. PCT/NL2013/050889, dated Mar. 18, 2014 (11 pages).

(Continued)

*Primary Examiner* — Joseph M Santos Rodriguez
(74) *Attorney, Agent, or Firm* — Bookoff McAndrews, PLLC

(57) ABSTRACT

The invention relates to a brachytherapy instrument comprising a body, wherein the body is provided with at least one marker comprising a material suitable to be visualized using an ultrasonic and/or magnetic resonance imaging technique. The invention further relates to an image acquisition system and a method of image acquisition.

18 Claims, 4 Drawing Sheets

(51) Int. Cl.
  *A61B 5/055* (2006.01)
  *A61N 5/10* (2006.01)
  *A61B 17/34* (2006.01)
  *A61B 90/96* (2016.01)
  *A61B 34/20* (2016.01)
  *A61B 90/00* (2016.01)

(52) U.S. Cl.
  CPC .......... *A61B 17/3468* (2013.01); *A61B 34/20* (2016.02); *A61B 90/39* (2016.02); *A61B 90/96* (2016.02); *A61N 5/1007* (2013.01); *A61N 5/1016* (2013.01); *A61N 5/1027* (2013.01); A61B 2034/2065 (2016.02); A61B 2090/3925 (2016.02); A61B 2090/3954 (2016.02); A61B 2090/3995 (2016.02)

(56) References Cited

U.S. PATENT DOCUMENTS

| | | | |
|---|---|---|---|
| 2002/0193677 A1 | 12/2002 | Thornton | |
| 2003/0153850 A1 | 8/2003 | Davis et al. | |
| 2004/0097804 A1 | 5/2004 | Sobe | |
| 2004/0124105 A1 | 7/2004 | Seiler et al. | |
| 2006/0132777 A1 | 6/2006 | Hubble et al. | |
| 2007/0038075 A1 | 2/2007 | Maschke | |
| 2008/0132782 A1 | 6/2008 | Rueckmann et al. | |
| 2010/0041938 A1 | 2/2010 | Stoianovici et al. | |
| 2010/0254897 A1* | 10/2010 | Frank ................. | A61N 5/1027 424/1.29 |

OTHER PUBLICATIONS

Kos, Sebastian et al., "Feasibility of Real-Time Magnetic Resonance-Guided Angioplasty and Stenting of Renal Arteries in Vitro and in Swine, Using a New Polytheretherketone-Based Magnetic Resonance-Compatible Guideware." Investigative Radiology, vol. 44, No. 4, Apr. 2009, 1-8 (8 pages).

Kos, Sebastian et al., "First Magnetic Resonance Imaging-Guided Aortic Stenting and Cava Filter Placement Using a Polyetheretherketone-Based Magnetic Resonance Imaging-Compatible Guideware in Swine: Proof of Concept," Cardiovascular and Interventional Radiology, vol. 32, Issue 3, May 2009, 514-521 (8 pages).

Kos, Sebastian et al., "MR-compatible polyetheretherketone-based guide wire assisting MR-guided stenting of iliac and supraaortic arteries in swine: Feasibility study," *Informa Healthcare Minimally Invasive Therapy*, vol. 19, No. 3, 2009, 1-8 (8 pages).

Li, Yangmei et al., "Development of an MRI/x-ray/ultrasound compatible marker for pre-operative breast tumour localization," *Physics in Medicine and Biology*, vol. 50, No. 14, 2005, 3349-3360 (12 pages).

"MagnaMedics Presents MagnaFy Technology at ISMRM 2009" *MAGNAFACTS Newsletter 2009*, Jul. 27, 2009 (1 page).

Response to Written Opinion for International Application No. PCT/NL2013/050889, dated Oct. 9, 2014 (10 pages).

Response to Second Written Opinion for International Application No. PCT/NL2013/050889, dated Dec. 29, 2014 (5 pages).

Second Written Opinion for International Application No. PCT/NL2013/050889, dated Dec. 2, 2014 (7 pages).

* cited by examiner

BRACHYTHERAPY INSTRUMENT, AN IMAGING SYSTEM AND A METHOD OF IMAGE ACQUISITION

CROSS-REFERENCE TO RELATED APPLICATIONS

This patent application is a U.S. national stage of International Patent Application No. PCT/NL2013/050889, filed Dec. 11, 2013, which claims the benefits of priority to NL Application No. 2009974, filed Dec. 12, 2012, and U.S. Provisional Application No. 61/737,313, filed Dec. 14, 2012, each of which is incorporated herein by reference in its entirety.

FIELD OF THE INVENTION

The invention relates to a brachytherapy instrument. In particular, the invention relates to an invasive, interstitial, intraluminal or intracavitary instrument.

The invention further relates to an image acquisition system. The invention still further relates to a method of image acquisition.

BACKGROUND OF THE INVENTION

In clinical practice brachytherapy applications are gaining importance. In the course of a brachytherapy treatment a radioactive source, usually a gamma emitter, is introduced into a target volume of a patient. The radioactive source may be introduced manually or using an afterloader device. Generally, the afterloader device is used for providing the radioactive source or sources inside the patient for a given (short) period of time inside pre-positioned catheters. In such a case, the gamma source may be a high dose rate source or a low dose rate source. Alternatively, the sources (seeds) may be provided inside the target volume of the patient for a prolonged (several hours) or permanent dwelling. Such sources may be low dose rate sources. Usually, a suitable radioactive source is accommodated in a catheter or a needle adapted for enabling introduction of the radioactive source into a vessel, a cavity, or a tissue volume.

It is a disadvantage of the contemporary brachytherapy that the actual source position in a patient is verified indirectly. For example, generally, suitable X-ray imaging may be used for determining the position of a source body or source bodies inside the patient (or a catheter introduced inside the patient). However, such an approach may be not sufficiently accurate or reliable in certain circumstances, for instance when a train of sources, such as active rods, is being provided, wherein the active rods are being interleaved with non-active spacers which fully imitate the geometry of the radioactive sources.

US2003/0153850 discloses a TRUS probe having glued stainless steel balls as fiducial markers, under ultrasound. Gadolinium impregnated materials are mentioned to be used as fiducial markers for MRI.

Us2010/0041938 discloses the use of contrast filled ellipses and contrast filled spheres as MRI/CT markers, at a frontal part of a needle delivery system.

SUMMARY OF THE INVENTION

It is an object of the invention to enable an improved source positioning and tracking during brachytherapy using an improved brachytherapy instrument.

To this end the brachytherapy instrument according to the invention comprises a body, wherein the body is provided with at least one marker comprising a material suitable to be visualized using an ultrasonic and/or magnetic resonance imaging technique.

In a preferred embodiment, the marker is a coating, i.e. has been coated. The coated marker (coating) can be manufactured with relatively high precision, with high accuracy, using relatively inexpensive means. The coating can e.g. be applied on existing brachytherapy instruments. In an embodiment, the marker coating can be used on flexible or bendable instruments. Also, the coating as such can be dimensioned or formed in a desired pattern or shape, particularly during application of the coating (i.e. during coating of the marker).

In a further embodiment, the marker coating is applied onto an external surface of the brachytherapy instrument, for example onto a section of that surface (leaving a remaining section of the surface free from the marker coating). One or more further layers may be applied onto the marker coating, for example to protect/shield the marker. Also, in an embodiment, the marker coating may be embedded in the instrument, for example within a wall of the instrument, and/or in a sandwich or multi-layer configuration.

It is found that positioning accuracy of the radioactive sources with respect to a target volume selected to be treated by means of radiotherapy may be substantially improved when the actual position of the source (e.g. seed) is being controlled directly. This direct control is enabled by providing the body of the radioactive source, or the body of the brachytherapy applicator with the marker and by carrying out real-time imaging of the target volume during positioning of the brachytherapy instrument inside the patient.

It will be appreciated that the marker may be provided on a dimensionally calibrated portion of the body, such as at a pre-determined distance from any suitable reference point. For example, the marker may be used to indicate a distal end of a relevant structure, such as a cavity in an applicator, or, alternatively, the marker may be used to indicate the relevant positions, such as source dwell positions, within the brachytherapy instrument.

It will be further appreciated that the brachytherapy instrument in the context of the present invention may be selected from a group consisting of:
 i) a radioactive source or a dummy source
 ii) a brachytherapy applicator having a cavity for accommodating one or more radioactive sources,
 iii) a cable for driving the radioactive source or the dummy source.
 iv) a rod, a tube, a reinforced rod, a reinforced tube, an obturator or guide wire which is used during insertion or during use of brachytherapy applicator.

It is further found that improved source positioning may be achieved when a cable adapted to transport the radioactive source or a dummy source is provided with the marker, enabling real-time tracking of the cable position. In particular, this feature is advantageous for enabling control of an adequate match between the radiotherapy planning geometry and the actual treatment geometry.

In a further embodiment of the brachytherapy instrument according to an aspect of the invention, the coated marker comprises or is manufactured from a material selected from the group consisting of: a ferromagnetic or a paramagnetic material, a hygroscopic material comprising ferromagnetic particles, a granulated material, an ultrasonic contrast material.

For a magnetic resonance visualization Iron Oxide, a ferromagnetic coating, and/or ink are found to be particularly suitable.

As an example, the coating can be an ink, the ink including Iron, or Iron Oxide, or both Iron and Iron Oxide. More particularly, the ink may include particles or clusters of Iron Oxide, or Iron, or both Iron and Iron Oxide.

In a preferred embodiment, the coating has been applied onto the instrument using a printing technique, for example (but not limited to) inkjet printing. Other coating techniques may be applied as well, for example brush-coating, clip-coating or spray-coating.

According to a preferred embodiment, providing good results, the coated marker includes aggregates/clusters of relatively small particles, for example aggregates/clusters of ferromagnetic particles. In an non-limiting embodiment, the aggregates may e.g. have external dimensions (e.g. width, diameter) in the range of about 40 to 100 nm, whereas the relatively small particles have external dimensions (e.g. width, diameter) smaller than 20 nm (e.g. about 14 nm) and for example larger than 1 nm.

For an ultrasonic visualization a suitable microencapsulation, such as microbubbles, added to an applicator surface may be used. It is found that these materials are particularly suitable for enabling accurate and reliable ultrasonic or magnetic resonance imaging of the brachytherapy instrument during treatment of a patient. For example, for an ultrasonic visualization, the marker coating can include or consist of Sono-coat™ of Encapson (www.encapson.eu).

It will be further appreciated that an embodiment of a brachytherapy catheter adapted with MRI means is known from US 2007/0038075. The known catheter comprises a Nuclear Magnetic Resonance (NMR) device accommodated at a distal end of the catheter for enabling local MR imaging.

However, it is a disadvantage of the known device that provision of the dedicated coils at the distal end of the catheter is required. This may be not compatible with dimensional constrains for the intravascular catheters. In addition, it is a disadvantage of the known device that the NMR arrangement provided at the distal end of the catheter is capable of performing MR imaging of the catheter tip only, i.e. the field of view is sub-centimeter. For brachytherapy applications having target volumes of more that 10 cm the catheter-based NMR system is not suitable.

The brachytherapy instrument according to the invention has an advantage that it enables exact control of the instrument's positioning inside the target volume wherein data about all expected source positions may be collected and corrected, if necessary.

In a still further embodiment of the brachytherapy instrument according to a further aspect of the invention the marker is provided on an outer surface of the said body, or is incorporated in a material of the body, or, when the body comprises a cavity, is provided on a surface forming the cavity. Alternatively, in a still further embodiment of the brachytherapy instrument, it may comprise a brachytherapy applicator provided with a hollow channel for receiving a further device. In this case the marker may be provided on the further device.

It is found that these marker positions are particularly suitable for enabling reliable real-time tracking and validation of the position of the brachytherapy instrument inside the patient.

For example, for an intracavitary applicator, the marker may be provided on the outer surface of the applicator and, preferably, may be also used for pre-positioning the applicator parts when mounting. For example, for a gynecological applicator comprising ovoids and an intra-uterine applicator, the ovoids and the intra-uterine applicator may be provided with markers not only for purposes of providing information about the position of the radioactive sources there within, but also for assisting a medical specialist in configuring the construction in a proper alignment.

Preferably, the coated marker is provided at pre-determined reference points suitable for carrying out dose planning for the brachytherapy treatment.

It is found that when the marker is provided on a brachytherapy applicator, and on the radioactive sources, the geometric match between the dose planning geometry and the actual geometry may be validated.

Preferably, the marker is fully or partially biocompatible. For example, the marker may be configured in such a way that at least an outer surface of the marker is biocompatible. It will be appreciated that in the present context, the term 'outer surface' relates to a surface of the marker which may come in contact with the surroundings, such as a patient's tissue or other parts of the brachytherapy instrument.

It is found that biocompatibility may be particularly important for brachytherapy instruments which are in direct contact with a system circulation, such as intravascular catheters, or for the brachytherapy instruments which are dwelling for a substantial time within a recipient, for example the interstitial needles accommodating the low dose brachytherapy sources.

In a further embodiment of the brachytherapy instrument the coated marker is provided as an area or as a pattern.

The pattern marker may be preferably provided with a rotational and/or a translational identifier. Due to this feature three-dimensional orientation of the brachytherapy instrument may be validated. It will be further appreciated that the marker may be provided on the radioactive source or on the dummy source directly. Preferably, the dummy source is provided with an extra indication that it comprises no radioactive material. This has an additional advantage that the tracing of radioactive sources may be carried out directly in a train of radioactive sources.

It will be further appreciated that the marker may be provided on a dummy source as well. This has an advantage that the medical specialist may optimize the treatment geometry using the dummy source under direct imaging conditions. Handlings of the dummy source are safe, as it does not emit radiation.

In a still further embodiment, the marker may be provided in the form of one or more rings, one or more lines, one or more dots, one or more alpha- or numerical images. Alternatively or additionally the pattern-shaped marker may have a form of a scale, a binary code, a bar code, or a dot code.

In a still further embodiment of the brachytherapy applicator the marker is at least two-dimensional having a variable content of the said material along at least one of its dimensions.

It is found that such configuration is advantageous as such marker may provide a directional information when the variable content of the marker material is imaged. For example, the marker may have a higher content of the imaging material at its extremity (distal or proximal) and a lower content of the imaging material in other areas. In this case it may be possible to verify orientation of the brachytherapy instrument in real time. For example, the marker may comprise elements which are spaced apart by the dimension of the (standard) line source. In applications where the total source is built from a number of active sources and dummy elements, the imaging data may provide a second independent view on the source length and/or source sequence. The binary code or the bar code are found to be particularly suitable for enabling automatic identification of the brachytherapy instrument. This feature may have a substantial added value in quality assurance of the procedure, as the user may utilize a per se known scanner for selecting a proper instrument for carrying out the prescribed therapy.

Those skilled in the art will readily appreciate that different embodiments of the above marker embodiments may be envisaged. In particular, the marker may be advantageously provided at pre-determined reference points suitable for carrying out dose planning for the brachytherapy treatment.

It is found that for the afterloader-based applications, it is particularly important to ensure that the source trajectory fully matches the prescribed source trajectory. In order to visualize the start and end trajectory point, the marker may be provided at different locations on the brachytherapy instrument. In particular, it is useful to provide the marker at the so-called dose reference points, that is, the points which are used for defining the source for dose planning purposes.

Because the afterloader treatment may be preceded by introduction of a dummy source it may be useful to check whether the dummy source fully follows the trajectory and/or the dose reference points. Should a substantial deviation be determined using the collected marker images, the treatment may be aborted and the brachytherapy instrument may be repositioned. Alternatively or additionally, the dose may be re-planned based on the actual trajectory of the source.

In a still further embodiment of the brachytherapy instrument according to a still further aspect of the invention the said marker material is adapted to be imaged using ultrasound imaging. In this case the marker material preferably comprises a foam, a roughened surface, an irregular surface, a micro-surface, a reflecting surface, spherical particles or a combination thereof.

An image acquisition system according to an aspect of the invention comprises a brachytherapy instrument according to the foregoing and an ultrasound or a magnetic resonance imaging apparatus. An embodiment of a suitable magnetic resonance imaging apparatus will be briefly discussed in further details with reference to FIG. 1. Those skilled in the art would readily appreciate which technical parameters and features are characteristic to a magnetic resonance imaging device or a ultrasound imaging device.

In an embodiment the image acquisition system comprises:
- a detector for detecting a response of the object to the said radiation;
- an imaging indicator arranged to define a position of the marker indicative of a region of interest;
- an imaging localizer arranged to determine a position and a dimension of the region of interest with respect to the marker;
- a control unit arranged to initiate data acquisition of the region of interest and/or the marker using the detector.

Preferably, the brachytherapy instrument is displaceable during data acquisition, the imaging localizer may be further arranged to determine an actual position of the displaceable marker provided on the said instrument.

It is found that by using the smart marker identification and tracking system introduction of the brachytherapy instrument inside the patient may be improved. Accordingly, for a displaceable the brachytherapy instrument, the imaging localizer may be further arranged to determine an actual position of the displaceable marker.

A method of image acquisition of a brachytherapy instrument according to a further aspect of the invention is recited in claims 21 and 22.

It will be further appreciated that the marker material which is visible on the images of a certain imaging modality, such as MR imager, may be further optimized to be also visible on the ultrasonic images. In particular, the marker may be a combination marker comprising separate markings, each being optimized for use with a specific imaging modality.

Also, an aspect provides a method for manufacturing an instrument according to the invention, the method including: coating the marker onto the instrument, for example utilizing an ink printing technique.

These and other aspects of the invention will be discussed with reference to Figures, wherein like reference numbers refer to like elements. It will be appreciated that the figures are provided for illustrative purposes only and may not be used for limiting the scope of the appended claims.

DETAILED DESCRIPTION OF THE DRAWINGS

Figure 1:
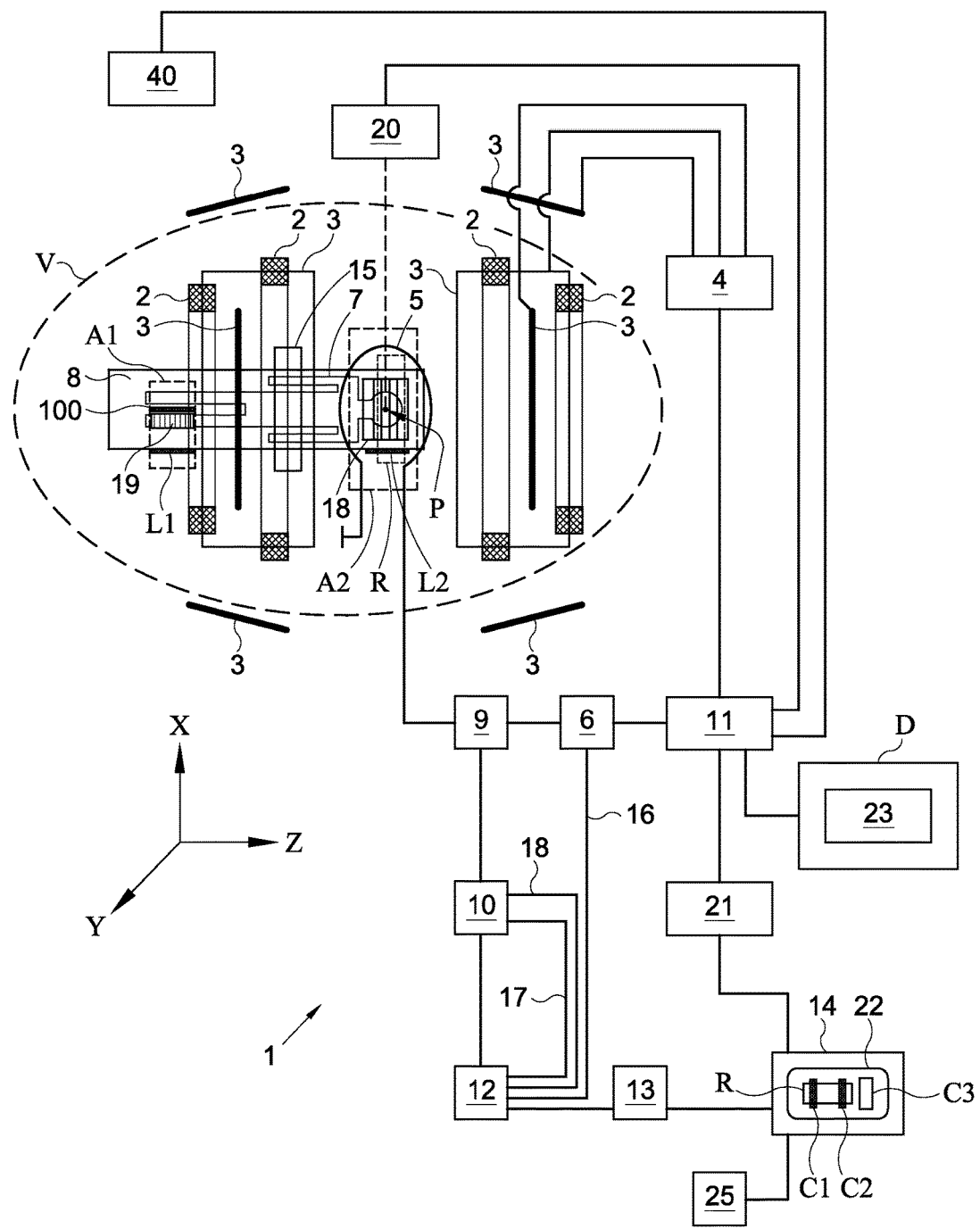
FIG. 1 presents in a schematic way an embodiment of a magnetic resonance imaging apparatus suitable for imaging a brachytherapy instrument provided with an MR visible marker.

FIG. 1 presents in a schematic way an embodiment of a magnetic resonance imaging apparatus suitable for imaging a brachytherapy instrument provided with an MR visible marker.

The magnetic resonance apparatus comprises a carrier 8 to position an object 7, notably a patient to be imaged in an imaging volume V, first magnet system 2, a second magnet system 3, a power supply unit 4, an RF transmitter and modulator 6, an RF transmitter coil 5, a plurality of receiver coils 18, 19, a transmitter-receiver circuit 9, a signal amplifier and demodulation unit 10, a processing unit 12, an image processing unit 13, a monitor 14, and a control unit 11. The first magnet system 2 serves to generate a steady magnetic field in the imaging volume V. The various gradient coils of the second magnet system 3 serve to generate additional magnetic fields having a gradient in the X, Y, Z directions, respectively. The Z direction of the coordinate system shown in FIG. 1 corresponds by convention to the direction of the steady magnetic field in the magnet system 2. The measuring coordinate system x,y,z to be used may be chosen independently of the X, Y, Z system illustrated in FIG. 1. In the context of the present application gradients are to be understood to mean temporary magnetic fields which are superposed on a steady magnetic field and cause a gradient in the steady magnetic field in three respective orthogonal directions.

The gradient coils 3 are fed by the power supply unit 4. The RF transmitter coil 5 serves to generate RF magnetic fields and is connected to the RF transmitter and modulator 6. The transmitter coil 5 is connected to the signal amplifier and demodulator unit 10 via the transmitter-receiver circuit 9. Receiver elements 18, 19, positioned at their respective locations L1, L2 on the carrier 8, are arranged to detect a response of the object to the RF magnetic fields. The receiver elements 18, 19 may comprise a suitable RF-antenna susceptible to magnetic resonance signals, or a receiver coil, notably a phased-array coil, or a coil element. The control unit 11 controls the RF transmitter and modulator 6, the power supply unit 4 and selects suitable coils 18, 19 to detect the response of the object 7 to the magnetic resonance excitation.

In order to enable an automatic selection of the suitable receiver coil 18, 19 and/or suitable coil elements of the receiver coils 18, 19, the control unit 11 is arranged to calculate a position of the region of interest R on the carrier 8 and use the respective locations of the receiver coils L1, L2. The position of the anatomical area of interest either A1, or A2 with respect to the carrier is automatically determined using, for example an action of a light visor 20, which is arranged to define a reference point P on the object 7, whereby said reference point is indicative of the anatomical area of interest. The position of the reference point with respect to the carrier 8 is determined automatically by the functionality of commonly used built-in light visors.

Alternatively, the automatic determination of the region of interest may be enabled using the determined position of a marker provided on a brachytherapy instrument 100. The dimension of the region of interest R is determined either automatically, for example by using a pre-stored imaging protocol defining the region of interest, by matching the acquired survey scan with an anatomical template, by manually defining the region of interest using a suitable user interface 22, or by an automatic marker tracking routine. The manual delineation of the region of interest is in this case preferably enabled by a suitable graphics pointing device 25, like a computer mouse.

It must be understood that in the magnetic resonance apparatus several related frames of reference exist. First, the magnet and gradient system has its common frame of reference with an origin, generally referred to as the isocenter. The imaging indicator, usually implemented as light visor, has a position, which is known by design of the magnetic resonance apparatus and is fixed in the magnet frame of reference. Secondly, the carrier has its own frame of reference, whose position is calibrated with respect to the frame of reference of the magnet during an installation procedure of the magnetic resonance apparatus, so that a simple transformation can be used to translate an actual position of the carrier, as measured, for example by a suitable software, into the frame of reference of the magnet. Third, a receiver coil has its own frame of reference and its location with respect to the carrier, the position of the coil elements being usually related to the origin of the receiver coil. Several coil arrangements are envisaged, namely a fixed coil, whereby its position to the carrier is known by design, for example due to suitable coil fixation means present on the carrier, or, alternatively, a displaceable coil, whereby its position can be established using automatic positioning means comprising suitable mechanical measures and/or suitable wireless positioning technology. Fourth, a patient is usually assigned its own frame of reference, related, for example to the selected anatomical area conceived to be imaged by means of the magnetic resonance apparatus. The position of the anatomical area is selectable by a user, whereby the user links the patient frame of reference to the frame of reference of the magnet. Thus, the relation between the frame of reference of the magnet and the frame of reference of the carrier and the frame of reference of the patient relates to the actual location of the carrier, whereby the transformation between the frame of reference of the carrier and the frame of reference of the receiver coil further relates the patient frame of reference to the coil location. Fifth, there is a frame of reference for the imaging region of interest within the selected anatomical area, which is defined by a suitable user (or is determined from the marker tracking routine) interface of the magnetic resonance apparatus, yielding, for example a graphic representation of the scan location with respect to a survey scan. The frame of reference of the region of interest is thus related to the patient frame of reference. Thus, in order to select a suitable receiver coil a simple transformation between the known frames of references Upon an event the dimension of the region of interest is established, the control unit 11 automatically calculates its position with respect to the carrier 8. After this, the control unit 11 addresses a look-up table 23, preferably stored in a suitable database D, said look-up table comprising respective dimensions of the receiver coils and respective locations L1, L2 of the receiver coils 18, 19 in the magnetic resonance imaging apparatus, notably on the carrier, or in the magnet bore. Preferably, for coil arrays the look-up table 23 comprises locations of respective coil elements within respective arrays, so that the coil elements may be individually selected. Alternatively, the locations of the receiver coils may be established in real-time using a per se known automatic positioning module 40. After this, the control unit 11 automatically determines which location of which receiver coils matches the position of the region of interest and selects the receiver coils accordingly. It is possible that the whole receiver coil is selected in this way, or a number of coil elements constituting a coil array. Preferably, the selection is being fed-back to the user on the user interface, whereby the selected coils C1, C2 are highlighted, for example on a survey scan. The non-selected coils are also presented using a different visualization method, for example as empty rectangles, or a dashed line. Still preferably, the user interface 22 is arranged to enable an adjustment of the automatic coils selection for the user. The adjustment may, for example be fulfilled using a suitable pointing device 25, like a computer mouse.

It will be appreciated that although FIG. 1 depicts a magnetic resonance imaging apparatus, another imaging modality, such as ultrasound imaging modality may be used. Those skilled in the art would readily appreciate how detection of the radiation-sensitive marker may be enabled per imaging modality.

Figure 2:
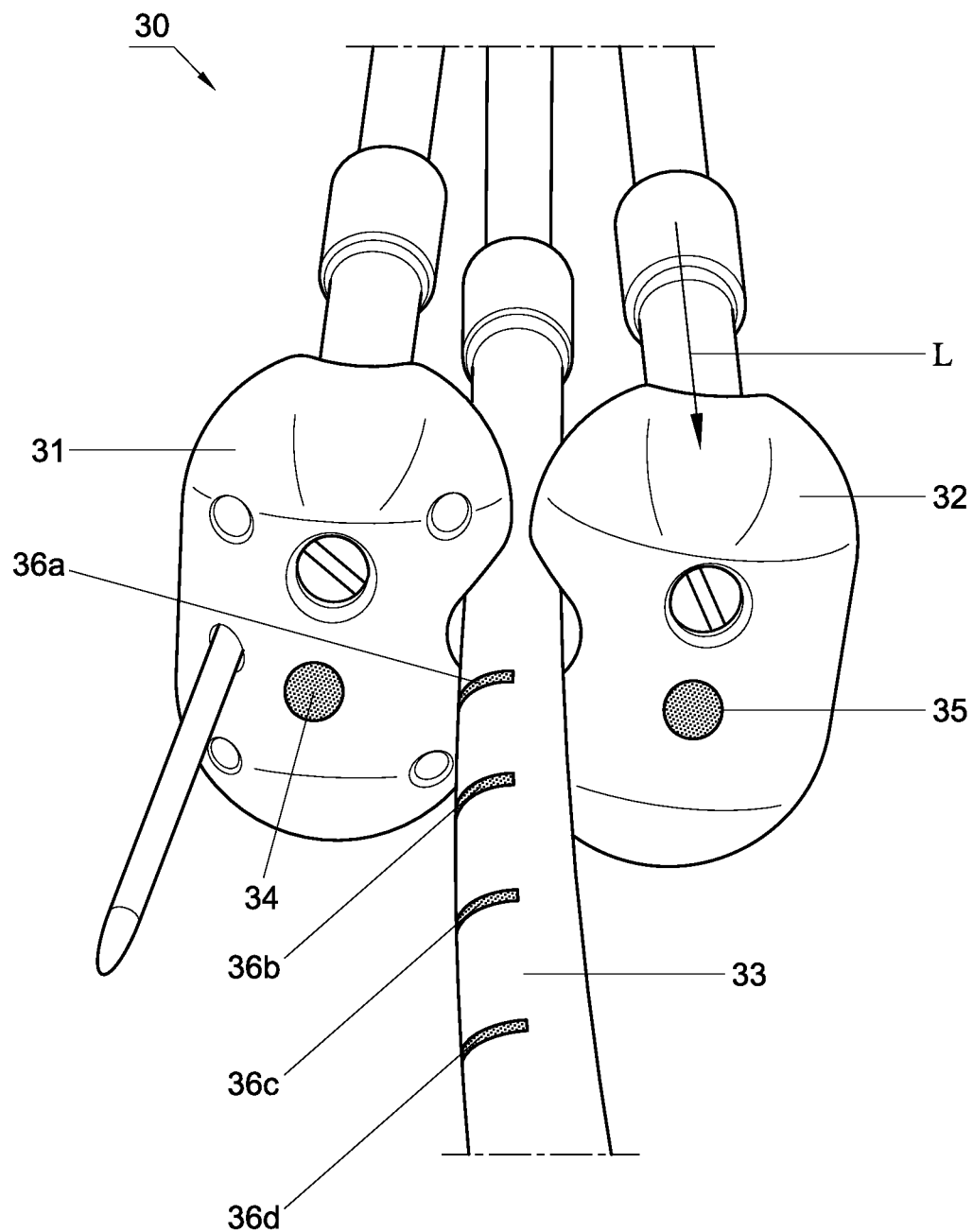
FIG. 2 presents a first embodiment of a brachytherapy instrument according to a first aspect of the invention.

FIG. 2 presents a first embodiment of a brachytherapy instrument 30 according to a first aspect of the invention. In this particular embodiment an intrauterine applicator 33 and two ovoids 31, 32 is depicted. In accordance with an aspect of the invention the individual parts of the brachytherapy instrument 30 are provided with an MR-visible marker. Particularly, the marker is a coating, e.g. an ink that has been coated onto or into the instrument 30.

In particular, the ovoids 31, 32, may be provided with a dot-like or area-like marker 34, 35, respectively. The markers 34, 35 may be about 1 cm in diameter and may be about 0.5-1.5 cm away from the distal end of the ovoid. Although in general the markers may be provided on the outer surface of the ovoid, it is also possible that the marker is provided inside the ovoid body. In a particular embodiment, the marker may be provided inside the ovoid substantially perpendicular to the longitudinal axis L. In case when the marker is dimensioned so that its edge is visible on the surface of the ovoid, it may be used for delineating the ovoids properly with respect to each other. Alternatively, the marker may be provided as a scale on the outer surface of the ovoids which simplifies their arrangement in the total configuration.

An embodiment of a marker configured as a scale is shown with respect to the inter-uterine applicator. The markings 36a, 36b, 36c, 36d are MR-visible and next to this function, they may provide absolute spatial information along the intra-uterine applicator. This is particularly useful when arranging the applicator inside the patient. For example, in situation when the depth of the uterus is known or is measured for the particular patient, the spatial information provided on the intra-uterine applicator is useful for avoiding an excessive insertion of the intra-uterine applicator into the patient's uterus.

It will be further appreciated that the MR-visible marker may be embodied as a suitable iron oxide material, which may be mixed with ink (having been coated at a location to be marked) thereby creating an artifact which indicates the position of the marker in an MR image.

In particular, in a further embodiment, a liquid column may be used as a primary marker, whereby the liquid column is distorted or is interrupted with the MR-contrast material as a secondary marker. Such artifact may be used for indicating a dwell position of the marker and, thus, the instrument, on the MR image.

Also, in a further embodiment, a said liquid column may be held in an enclosure (e.g. a tube, hose, needle, or another suitable liquid column holding structure), wherein the enclosure may be provided with one or more coated markers (e.g. a said ink), as additional/secondary markers with respect to the liquid column (primary marker) as such.

Figure 3:
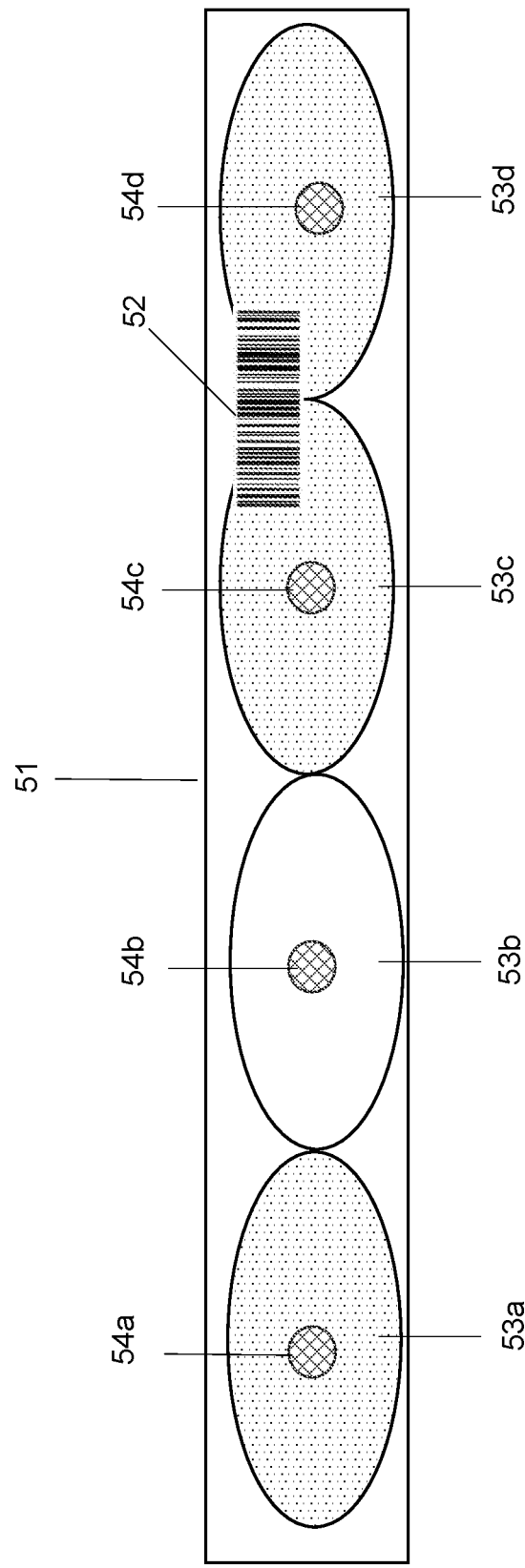
FIG. 3 presents a further embodiment of a brachytherapy instrument according to a further aspect of the invention.

FIG. 3 presents a further embodiment of a brachytherapy instrument according to a further aspect of the invention. In this particular embodiment the brachytherapy instrument 51 may be embodied by a catheter, a needle, a guide wire or by any other substantially longitudinal structure. In accordance with the present embodiment, the brachytherapy instrument 50 is provided with a coated marker, being a bar code 52, which may be suitable for enabling easy automatic identification in use. The bar code is preferably machine-readable for automation purposes. It is found that this feature may be advantageous for improving safety of the interstitial applications. Because the marker 52 is MR-visible, selection of the proper instrument may be further confirmed using MR means.

In addition, the brachytherapy instrument 51 may be provided with further coated markers 54a, 54b, 54c, 54d which may be suitably provided at reference positions used for carrying out dose planning in brachytherapy. For example, in case when the radioactive source is build-up from several active components 53a, 53c, 53d separated by an inactive component 53b, the markers 54a, 54b, 54c, 54d may be provided at expected centers of the individual sources when they are dwelling inside the brachytherapy instrument 51.

Accordingly, when the brachytherapy instrument is provided inside the patient an image of the markers is acquired together with the sources and the instrument. Using suitable image processing techniques it is possible to investigate whether the actual centers of the sources fully correspond with the planned centers using the reference markers 54a, 54b, 54c, 54d. In addition, it is possible to automatically confirm that the source sequence 53a, 53b, 53c, 53b is arranged properly, in particular whether the active segments and the inactive segments are located at their prescribed dwell locations.

Figure 4:
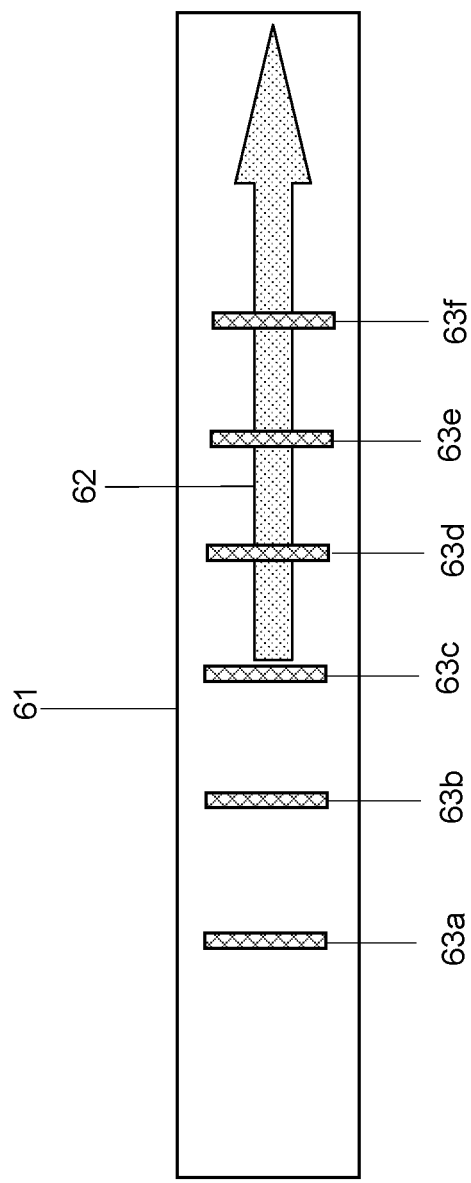
FIG. 4 presents a still further embodiment of a brachytherapy instrument according to a still further aspect of the invention.

FIG. 4 presents a still further embodiment of a brachytherapy instrument 61 according to a still further aspect of the invention. In this particular embodiment the marker is a composite marker comprising an orientation element 62 and a scale 63a, 63b, 63d, 63e, 63f. The orientation element may be provided to assist the user in maneuvering the brachytherapy instrument inside the patient. The markers 63a, 63b, 63d, 63e, 63f may be located at the respective centre of the dwell positions of the radioactive source. Alternatively or additionally, the plurality of markers may be optimized to be visible using different imaging modalities, such as MR and ultrasound.

It will be appreciated that the term 'brachytherapy instrument' shall not be limited to the particular examples described with reference to drawings. Any device, applicator, holder and so on usable in the field of brachytherapy may be provided with a marker as is described with reference to the foregoing.

In addition, while specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

For example, a said coating can be applied in different ways, for example via a printing technique, via spray coating, clip coating, brush-coating, contact-coating, ink-jet coating, or differently, as will be appreciated by the skilled person. A coating, applied in such a way, can be relatively thin, e.g. having a thickness that is significantly smaller (e.g. at least 10 times smaller) than a width of the coating (the width being measured in a direction normal to the measuring said thickness).

The invention claimed is:

1. A brachytherapy instrument for insertion into a cavity of a patient for administering radioactive treatment to the patient, the instrument comprising:
   a body having an inner channel configured to receive a radioactive source for administering the radioactive treatment;
   a first marker located on an outer surface at a first location of the body and formed of a coating of ferromagnetic material; and
   a second marker formed of a material different than the ferromagnetic material of the first marker and located on the outer surface of the body at a second location, wherein the first marker is configured to create a first artifact in a magnetic resonance image that is indicative of a position of the first marker when the instrument is inserted in the cavity of the patient.

2. The instrument of claim 1, wherein at least one of the first marker or the second marker includes a plurality of markers.

3. The instrument of claim 2, wherein at least one of the first marker or the second marker includes a marker for positioning the instrument within the cavity of the patient or for positioning a source within the patient.

4. The instrument of claim 2, wherein at least some of the plurality of markers are spaced apart from one another at a pre-determined interval.

5. The instrument of claim 4, wherein the spaced-apart markers correspond to intended dwell positions of a source within the channel.

6. The instrument of claim 1, wherein the body further includes (i) an intrauterine applicator extending along a longitudinal axis and (ii) an ovoid, and wherein the first marker is located on an outer surface of the ovoid and the second marker is located on an outer surface of the intrauterine applicator.

7. The instrument of claim 6, wherein the second marker comprises a plurality of markers located on the outer surface of the intrauterine applicator.

8. The instrument of claim 6, wherein the ovoid is laterally spaced relative to the intrauterine applicator.

9. The instrument of claim 1, wherein the second marker comprises a liquid marker formed of a liquid column contained in an enclosure, wherein the enclosure includes a coated marker, and wherein the liquid marker is configured to create a second artifact in the magnetic resonance image that is indicative of a position of the liquid marker in the cavity of the patient.

10. The instrument of claim 1, wherein the first marker or the second marker is located on a distal end of the body.

11. The instrument of claim 1, wherein the first marker comprises a first portion having a first content of ferromagnetic material and a second portion having a second content of ferromagnetic material, wherein the first content is different than the second content, and wherein the difference between the first and the second content is configured to provide directional information about the instrument in the magnetic resonance image.

12. The instrument of claim 1, wherein the instrument is included as part of a kit, wherein the kit further includes a dummy source configured for insertion into the channel, and wherein the dummy source includes a dummy source marker.

13. The instrument of claim 1, wherein the second marker is an ultrasound marker, wherein the ultrasound marker is configured to create a second artifact in an ultrasound image that is indicative of a position of the ultrasound marker when the instrument is inserted in the cavity of the patient.

14. The instrument of claim 13, wherein the ultrasound marker is formed of a coating of microencapsulations.

15. The instrument of claim 1, wherein the instrument is a brachytherapy applicator.

16. A brachytherapy instrument for insertion into a cavity of a patient for administering radioactive treatment to the patient, the instrument comprising:
    a body having an inner channel dimensioned to receive a radioactive source for administering the radioactive treatment;
    a first marker formed of a first material located on an outer surface of the body and configured to create a first artifact in a magnetic resonance image; and
    a plurality of discrete second markers formed of a second material, different than the first material, and spaced apart from one another on the outer surface of the body along a longitudinal axis of the body, wherein the plurality of discrete second markers are configured to create a plurality of second artifacts in a medical image that are indicative of a plurality of dwell positions of a source.

17. The instrument of claim 16, comprising a plurality of first markers.

18. The instrument of claim 16, wherein the plurality of discrete second markers are located on an outer surface of an intrauterine tube.

* * * * *

UNITED STATES PATENT AND TRADEMARK OFFICE
CERTIFICATE OF CORRECTION

PATENT NO. : 10,226,232 B2
APPLICATION NO. : 14/651541
DATED : March 12, 2019
INVENTOR(S) : Cor Van de Wardt, Wilhelmus van Erp and Luite Visscher It is certified that error appears in the above-identified patent and that said Letters Patent is hereby corrected as shown below:

On the Title Page

Item (72), in the Inventors section, delete "Petra" and insert -- Petrus --.

Signed and Sealed this
Fourteenth Day of January, 2020

Andrei Iancu
*Director of the United States Patent and Trademark Office*